United States Patent
Ash

[11] Patent Number: 5,919,369
[45] Date of Patent: *Jul. 6, 1999

[54] HEMOFILTRATION AND PLASMAFILTRATION DEVICES AND METHODS

[75] Inventor: Stephen R. Ash, Lafayette, Ind.

[73] Assignee: Hemocleanse, Inc., West Lafayette, Ind.

[ * ] Notice: This patent is subject to a terminal disclaimer.

[21] Appl. No.: 08/683,678

[22] Filed: Jul. 16, 1996

Related U.S. Application Data

[63] Continuation-in-part of application No. 08/180,080, Jan. 11, 1994, Pat. No. 5,536,412, which is a continuation-in-part of application No. 07/832,080, Feb. 6, 1992, Pat. No. 5,277,820.

[51] Int. Cl.$^6$ ........................... B01D 61/00; B01D 63/02; B01D 61/26

[52] U.S. Cl. .................. 210/645; 210/195.1; 210/195.2; 210/257.1; 210/258; 210/321.78; 210/321.79; 210/321.8; 210/321.87; 210/321.88; 210/321.89; 210/433.1; 210/434; 210/435; 210/500.23; 210/646; 210/650; 210/651; 210/660; 210/805

[58] Field of Search ..................................... 210/644, 645, 210/646, 650, 651, 660, 767, 805, 929, 195.1, 195.2, 205, 321.78, 257.1, 321.79, 258, 321.8, 321.87, 321.88, 321.89, 433.1, 435, 434, 500.23; 422/101; 436/178; 604/4, 5, 6

[56] References Cited

U.S. PATENT DOCUMENTS

| | | |
|---|---|---|
| 4,056,467 | 11/1977 | Christen et al. |
| 4,071,444 | 1/1978 | Ash et al. |
| 4,247,393 | 1/1981 | Wallace ................................... 210/638 |
| 4,348,283 | 9/1982 | Ash. |
| 4,375,414 | 3/1983 | Strahilevitz ............................. 210/638 |
| 4,402,694 | 9/1983 | Ash et al. |
| 4,581,141 | 4/1986 | Ash ......................................... 210/502 |
| 4,661,246 | 4/1987 | Ash ........................................... 210/87 |
| 4,714,556 | 12/1987 | Ambrus et al. .......................... 210/638 |
| 4,770,784 | 9/1988 | Davis et al. ............................. 210/638 |
| 5,078,885 | 1/1992 | Matsumura .............................. 210/632 |
| 5,211,850 | 5/1993 | Shettigar et al. ........................ 210/645 |
| 5,277,701 | 1/1994 | Christie et al. .............................. 604/4 |
| 5,277,820 | 1/1994 | Ash ......................................... 210/646 |
| 5,328,614 | 7/1994 | Matsumura .............................. 210/632 |
| 5,536,412 | 7/1996 | Ash ......................................... 210/645 |
| 5,626,759 | 5/1997 | Krantz et al. ............................ 210/645 |
| 5,753,227 | 5/1998 | Strahilevitz ............................. 210/660 |

OTHER PUBLICATIONS

Malchesky, P.S., Wojcicki, J., Horiuchi, T., Lee, J.M., and Nosé, "Membrane Separation Processes For Macromolecule Removal", *Plasmapheresis*, pp. 51–67 (1983), ISAO Press, Cleveland.

Macias, M.D., Ph.D., William L., Mueller, Pharm.D., Bruce A., Scarim, Pharm.D., Sheila Kelly, Robinson, M.D., Merryn, and Rudy, M.D., David W., "Continuous Venovenous Hemofiltration: An Alternative To Continuous Arteriovernous Hemofiltration And Hemodiafiltration In Acute Renal Failure", *Amer. J. Kidney Diseases*, vol. OVIII, No. 4, pp. 451–458 (Oct., 1991).

(List continued on next page.)

*Primary Examiner*—John Kim
*Attorney, Agent, or Firm*—Woodard, Emhardt, Naughton, Moriarty & McNett

[57] ABSTRACT

Disclosed are preferred devices and methods which provide extracorporeal treatment of blood or other fluids for effective plasmafiltration or hemofiltration alone or in combination with dialysis. Preferred devices combine plasmafiltration and dialysis devices, and are designed to circulate separate sorbent suspensions through the respective devices and minimize clogging in sorbent circulation loops, including the provision of a shaker or vibrator device operable to vibrate the suspension used in the plasmafiltration device.

25 Claims, 8 Drawing Sheets

OTHER PUBLICATIONS

Castino, F., Scheucher, P.S., Malchesky, P.S., Koshino, I., and Nosé, Y., "Microemboli–Free Blood Detoxification Utilizing Plasma Filtration", *Trans. Amer. Soc. Artif. Int. Organs*, vol. XXII, pp. 637–645 (1976).

Christie, D.J., Howe, R.B., Lennon, S.S., and Sauro, S.C., "Treatment Of Refractoriness To Platelet Transfusion By Protein A Column Therapy", *Transfusion*, vol. 33, No. 3, pp. 234–242 (1993).

Howe, Robert B. and Christie, Douglas J., "Protein A Immunadsorption Treatment In Hematology: An Overview", *J. Clinical Apheresis*, vol. 9, pp. 31–32 (1994).

Snyder, Jr., Harry W., Cochran, Sharon K., Balint, Jr., Joseph P., Bertram, Juergen H., Mittelman, Abraham, Guthrie, Jr., Troy H., Jones, Frank R., "Experience With Protein A–Immunoadsorption In Treatment–Resistant Adult Immune Thrombocytopenic Purpura", *Blood*, vol. 79, No. 9, pp. 2237–2245 (May 1, 1992).

*Alternatives In Uremia Therapy*, pp. 883–897 (undated).

Maeda, Kenji, Kobayakawa, Hiroyuki, Fujita, Yoshiro, Takai, Ichiro, Morita, Hiroyuki, Emoto, Yutaka, Miyazaki, Takashi, and Shinzato, Takahiro, "Effectiveness Of Push/Pull Hemodiafiltration Using Large–Pore Membrane For Shoulder Joint Pain In Long–Term Dialysis Patients", *Artificial Organs*, vol. 14, No. 5, pp. 321–327 (1990).

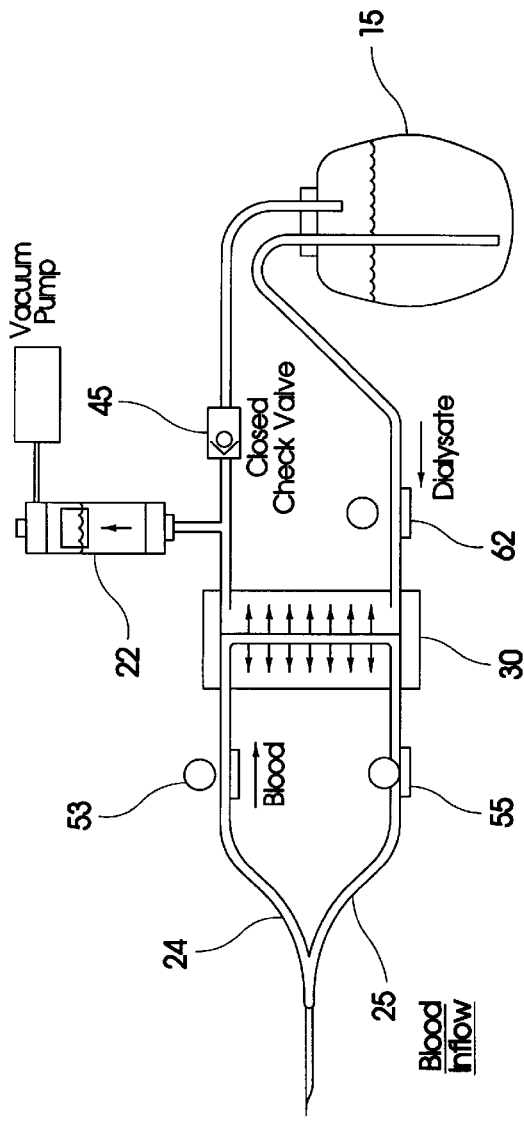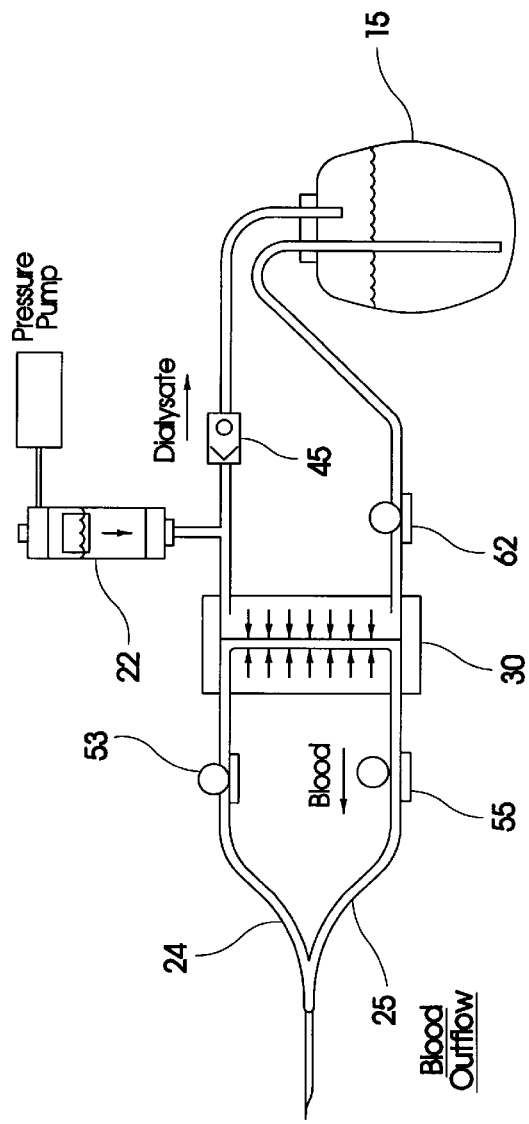

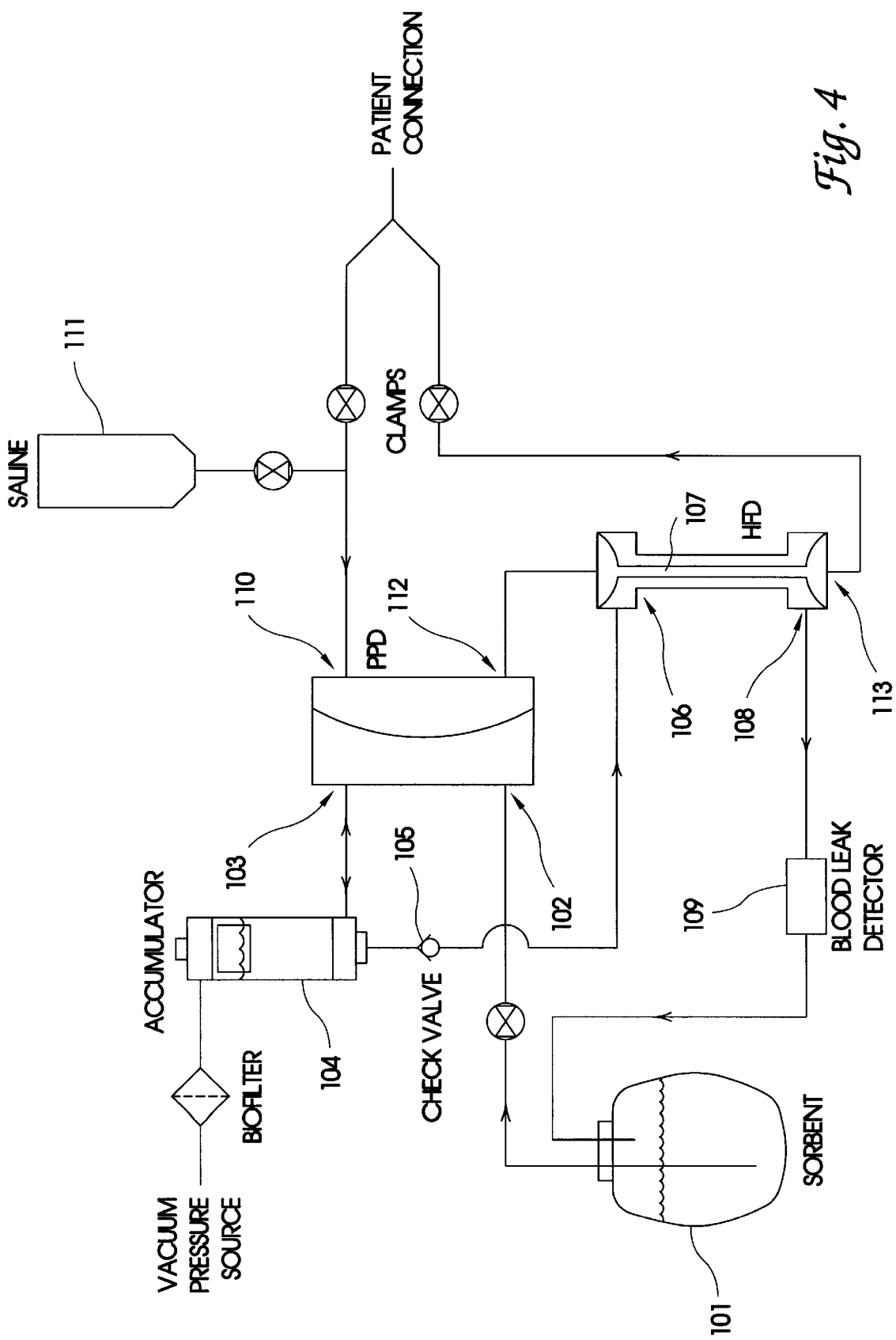

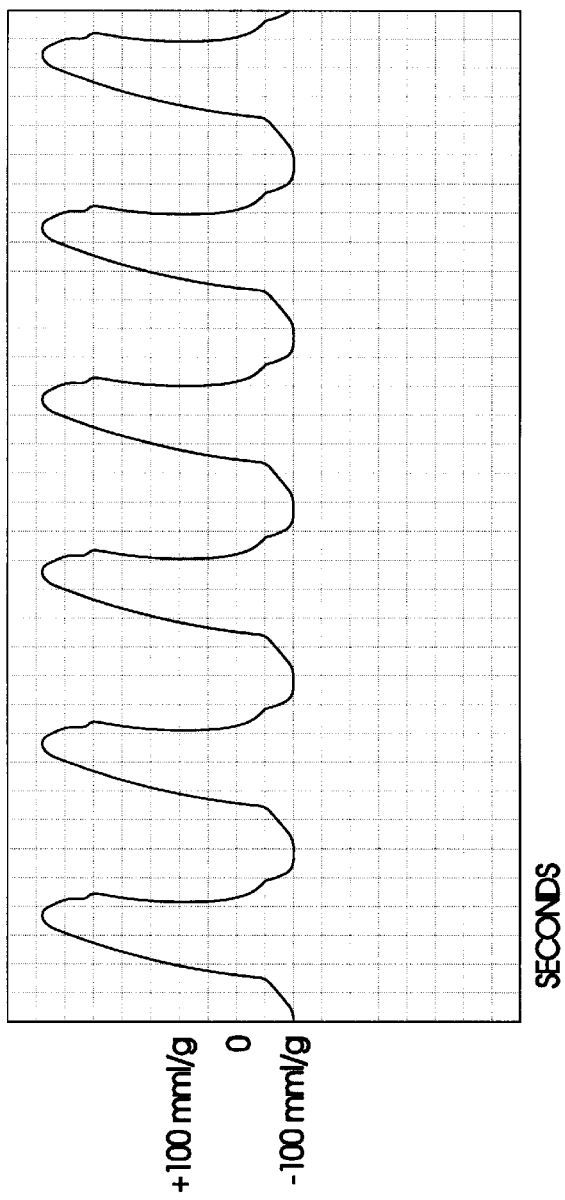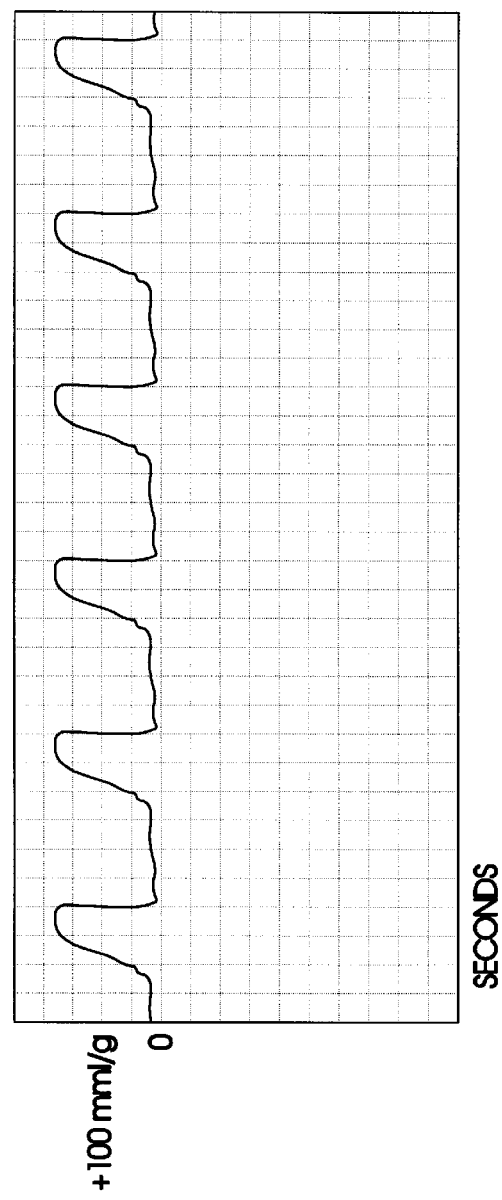

HEMOFILTRATION AND PLASMAFILTRATION DEVICES AND METHODS

REFERENCE TO RELATED APPLICATION

This is a continuation-in-part application of U.S. patent application Ser. No. 08/180,080 filed Jan. 11, 1994, now issued as U.S. Pat. No. 5,536,412, which is hereby incorporated herein by reference in its entirety, which is a continuation-in-part of U.S. patent application Ser. No. 07/832,080 filed Feb. 6, 1992, now issued as U.S. Pat. No. 5,277,820.

BACKGROUND OF THE INVENTION

This invention generally relates to devices and methods for extracorporeally treating blood or blood fractions such as blood filtrate or plasma to selectively remove toxins therefrom.

By way of background, extensive efforts have been made to discover safe and effective methods for removing toxins from patients by extracorporeal treatment of their blood. These efforts have included many studies directed to methods for extracorporeal treatment of hepatic failure due to infection, cirrhosis, toxin damage or other causes. Many methods have been proposed with the goal of removing small molecular toxins, protein-bound molecules or larger molecules thought to be responsible for the coma and illness of hepatic failure. Thus far, evidence has been presented supporting adverse effects caused by non-protein bound small molecules such as ammonia, phenols, mercaptans, short chain fatty acids, aromatic amino-acids, neural inhibitors (GABA, glutamate), false neural transmitters (octopamine) and bile salts. Among these, phenols and mercaptans, along with bilirubin and bacterial endotoxins, also occur as strong protein-bound toxins and are thus more difficult to effectively remove from the blood. In addition, there are a variety of middle molecular weight toxins of liver failure having molecular weights of about 300 to about 10,000 which are difficult to effectively remove.

As to specific modes of treatment, those previously proposed and used have included blood perfusion over heterogeneous liver pieces or past membranes which contact hepatocytes. Also proposed and used have been hemoperfusion through columns of coated activated carbon or macroreticular resins, blood exchange, plasmapheresis with plasma replacement, plasmapheresis with plasma perfusion through bilirubin-binding and aromatic amino acid-binding sorbents, standard hemodialysis, standard hemodialysis with an amino acid dialysate and plasma exchange, high permeability hemodialysis, dialysis with charcoal-impregnated membranes, continuous hemofiltration, peritoneal dialysis, oral sorbents and many other therapies.

While some of these previously proposed treatments have produced neurological improvement in stage 2 or 3 coma and have aided hepatic regeneration after injury, they have not provided much clinical improvement in patients in stage 4 coma on respirators. Additionally, these diverse treatments each produce adverse effects on the patient, offsetting benefits. See, generally, Ash, S. R., Treatment of Acute Hepatic Failure With Encephalopathy: A Review, *Int. J. of Artif. Organs,* Vol. 14, pp. 191–195 (1991).

For example, although daily charcoal hemoperfusion has been shown to provide neurologic and physiologic improvement of patients with hepatic failure and coma, Winchester, J. F., Hemoperfusion, in Replacement of Renal Function by Dialysis (Maher, J. F., ed.), Dordrecht:Kluwer Academic Publishers, pp. 439–459, (1989), hemoperfusion nevertheless requires systemic anticoagulation and also depletes coagulation factors and platelets from the blood. Moreover, the relatively large sorbent granules used in hemoperfusion columns have limited surface area (about 1000–10,000 $m^2$). Consequently, the available sorbent surface area is saturated within a few hours, clearance of bound chemicals rapidly diminishes, and a new column must be used.

Furthermore, clinical benefits of charcoal hemoperfusion may be offset by deleterious effects of bioincompatibility. In one instance, a controlled study of patients with fulminant hepatic failure, all treated with aggressive intensive care including intracerebral pressure monitoring, demonstrated that patients treated by hemoperfusion had a generally lower survival rates than those treated with aggressive intensive care alone. The only exception was noted in patients having fulminant hepatic failure due to hepatitis A or B, for whom there was reported a "trend toward improved survival" when treated with charcoal perfusion. O'Grady, J. G. et al., Controlled Trials of Charcoal Hemoperfusion and Prognostic Factors in Fulminant Hepatic Failure, *Gastroenterology,* Vol. 94, pp. 1186–92 (1988).

As mentioned, standard hemodialysis (i.e. dialysis of blood against only a dialysate solution) has also been studied as a possible treatment for hepatic failure. However, benefits of hemodialysis may be similarly obscured by removal of substances (e.g. urea) known not to be toxins of hepatic failure. Additionally, hemodialysis requires the use of large volumes of dialysate solution which limits the mobility and increases the complexity of the machines, or alternatively, it requires the provision of a sorbent column to "regenerate" the dialysate.

In light of this extensive background, there remain needs for improved devices and methods for the extracorporeal treatment of blood or of blood fractions to effectively remove toxins, including both soluble and protein-bound toxins. The present invention addresses these needs.

SUMMARY OF THE INVENTION

The present invention provides a unique filtration process (e.g. a hemofiltration or plasmafiltration process) which is highly effective in removing protein-bound and middle molecular weight toxins. The inventive process includes the steps of passing a fluid, such as blood, containing protein-bound or middle molecular weight blood toxins, through the interior of a hollow fiber membrane, and during the passage of blood, circulating a sorbent suspension against exterior surfaces of the hollow fiber membrane. As a further step, during the passage of blood and circulation of sorbent suspension, the plasma fraction of the blood is caused to alternately exit and re-enter the interior of the membrane. Thereby, blood plasma contacts the sorbent suspension upon exit from the interior of the membrane, so as to effectuate removal of the toxins from the blood. This embodiment of the invention is applied with preference to whole blood; however, the invention is not so limited, as it will be applicable as well to the treatment of other fluids containing middle molecular weight and/or protein bound blood toxins, e.g. blood fractions such as isolated blood plasma or other blood toxin-containing fluids such as blood filtrate.

Another inventive process includes the steps of passing a fluid, such as blood, containing protein-bound or middle molecular weight blood toxins, through the interior of a hollow fiber membrane, and during the passage of blood, circulating a sorbent suspension against exterior surfaces of the hollow fiber membrane. As a further step, during the passage of blood and circulation of sorbent suspension, the sorbent suspension is caused to vibrate, and, optionally, pressure differentials are periodically created across the membrane to cause the fluid (e.g. blood) or a fraction thereof to alternately exit and re-enter the interior of the membrane. Thereby, the sorbent suspension is beneficially mixed so as to decrease aggregation or clogging around the membrane, and blood plasma contacts the sorbent suspension upon exit from the interior of the membrane, so as to effectuate removal of the toxins from the blood.

Another preferred embodiment of the present invention provides a device which is highly effective for removing protein-bound or middle molecular weight toxins from fluids such as blood, blood plasma or blood filtrate. The preferred device of the invention includes a hollow fiber membrane, and a pump fluidly connected to the interior of the hollow fiber membrane and adapted to pass blood (or another fluid containing the toxins) through the interior. The device further includes a chamber surrounding the hollow fiber membrane, the chamber also being fluidly connected to a supply of sorbent suspension containing solid particulate adsorbent. A pump is adapted to circulate the sorbent suspension through the chamber and against exterior surfaces of the hollow fiber membrane. Means for causing the blood or other fluid or a fraction thereof passing through the interior of the membrane to alternately exit and re-enter the interior of the hollow fiber membrane are also provided.

Another preferred embodiment of the present invention provides a device which is highly effective for removing protein-bound or middle molecular weight toxins from fluids such as blood, blood plasma or blood filtrate. The preferred device of the invention includes a hollow fiber membrane, and a pump fluidly connected to the interior of the hollow fiber membrane and adapted to pass blood (or another fluid containing the toxins) through the interior. The device further includes a chamber surrounding the hollow fiber membrane, the chamber also being fluidly connected to a supply of sorbent suspension containing solid particulate adsorbent. A pump is adapted to circulate the sorbent suspension through the chamber and against exterior surfaces of the hollow fiber membrane, and means are provided for causing the sorbent suspension to vibrate during its circulation. Optionally, pressure-driven means are provided for causing the blood or other fluid or a fraction thereof passing through the interior of the membrane to alternately exit and re-enter the interior of the hollow fiber membrane are also provided.

Still another preferred embodiment of the present invention provides a method for circulating a sorbent suspension in a device for extracorporeal treatment of blood or a blood fraction. The method of the invention includes a step of providing the device having a sorbent circulation circuit and a blood circulation circuit separated by membranes, the membranes being compliantly formed to expand and contract in response to alternating positive pressure and negative pressure applied to the sorbent circulation circuit and thereby advance a sorbent suspension through the sorbent suspension circulation circuit. An accumulator reservoir is provided and fluidly connected to the sorbent circulation circuit, and is operable to alternately accumulate and expel sorbent suspension in response to alternating negative pressure and positive pressure applied to the accumulator reservoir. Thereby, the accumulator reservoir communicates the alternating negative and positive pressure to the sorbent circulation circuit. The method further includes applying alternating positive pressure and negative pressure to the accumulator reservoir so as to communicate the same to the sorbent circulation circuit and cause the compliant membranes to expand and contract, whereby the sorbent suspension is advanced through the sorbent suspension circuit.

Still another preferred embodiment of the invention provides a device for extracorporeal treatment of blood or a blood fraction. This device has a sorbent circulation circuit and a blood circulation circuit separated by membranes, wherein the membranes are compliantly formed to expand and contract in response to alternating positive pressure and negative pressure applied to the sorbent circulation circuit and thereby advance a sorbent suspension through the sorbent suspension circulation circuit. An accumulator reservoir is fluidly connected to the sorbent circulation circuit and operable to alternately accumulate and expel sorbent suspension in response to alternating negative pressure and positive pressure applied to the accumulator reservoir, the accumulator reservoir thereby communicating the alternating negative and positive pressure to the sorbent circulation circuit. The device also includes a source of positive pressure and of negative pressure fluidly connected to the accumulator reservoir. When alternating positive pressure and negative pressure are alternately applied to the accumulator reservoir, the same is communicated to the sorbent circulation circuit to cause the compliant membranes to expand and contract, whereby the sorbent suspension is advanced through the sorbent suspension circuit.

The invention provides methods and devices by which greater removal of protein-bound and middle molecular weight blood toxins from blood, blood plasma or blood filtrate can be achieved, and whereby efficient circulation of sorbents on the sorbent side of a variety of different types of extracorporeal treatment devices is effectuated. Additional objects, features and advantages of the present invention will be apparent from the description which follows.

BRIEF DESCRIPTION OF THE DRAWINGS

FIGS. 3A and 3B are schematic representations of the mechanics of operation of the preferred direct pressure/vacuum operated dialysis system of FIG. 1.

FIG. 4 is a schematic representation of the hydraulic circuit of a combined device incorporating the system of FIG. 1 in series with a hollow fiber plasmafilter.

FIG. 5(a) shows the blood-side pressure curve between the system of FIG. 1 and the plasmafilter in the combined device of FIG. 4, during several inflow-outflow cycles.

FIG. 5(b) shows the sorbent-side pressure curve within the plasmafilter membrane package of the combined device of FIG. 4. Mean blood-sorbent pressure difference is approximately zero.

DESCRIPTION OF THE PREFERRED EMBODIMENTS

Figure 1:
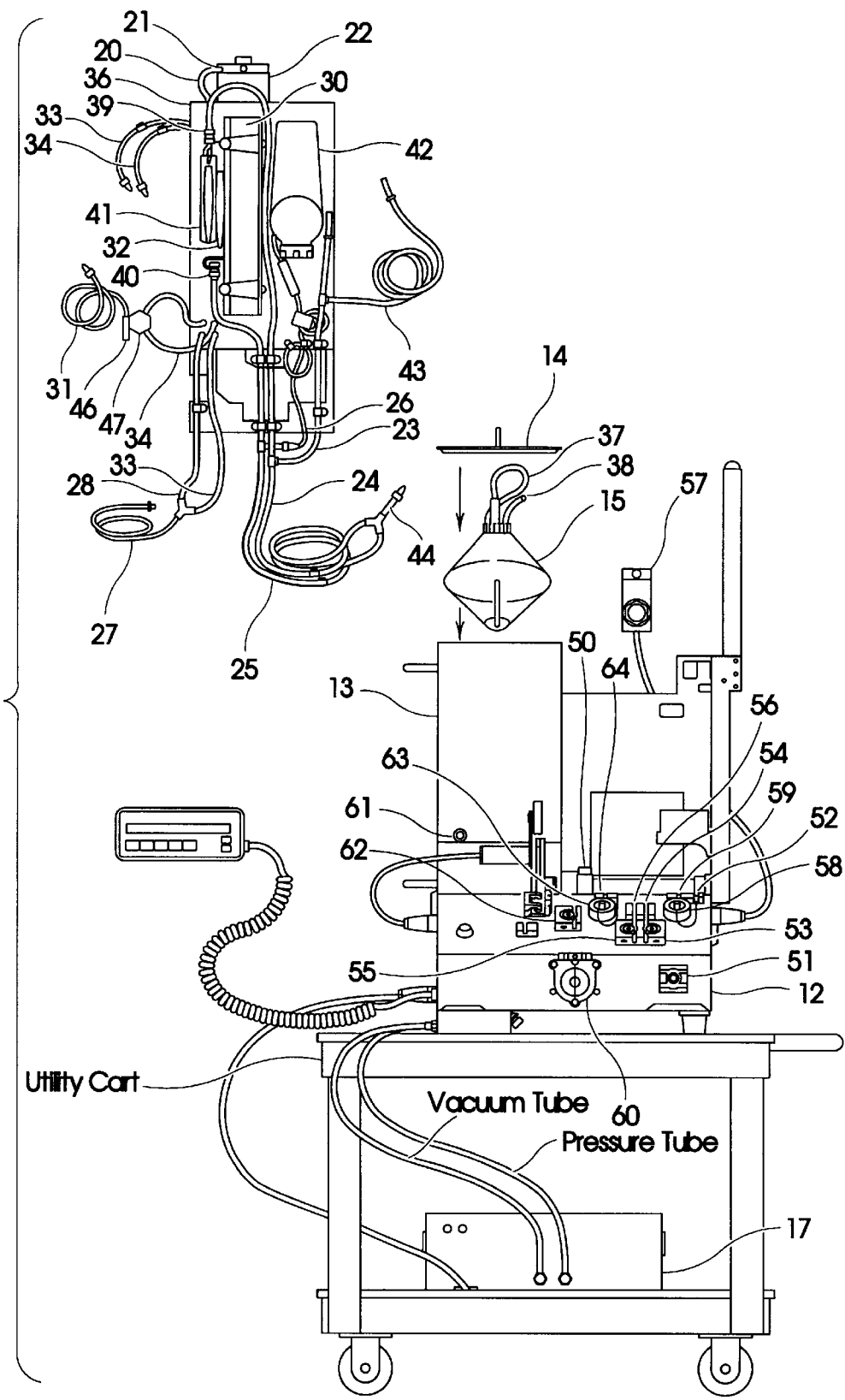
FIG. 1 is a perspective view of a preferred pressure/vacuum operated dialysis system which can be used in the invention.

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, one preferred embodiment of this invention relates to a method which can be used for extracorporeal treatment of blood or a blood fraction by filtration, e.g. plasmafiltration (wherein plasma is filtered across a membrane) or hemofiltration (wherein middle molecular weight molecules (i.e. having molecular weights of about 300 to about 10,000) are filtered across a membrane), in a manner which provides the safe, consistent and effective removal of toxins, including protein-bound blood toxins and middle molecular weight blood toxins. This filtration can be used alone, or in connection with dialysis of the blood or blood fraction, for example using dialysis devices and methods as described in my prior U.S. patent application Ser. No. 07/832,080 filed Feb. 6, 1992, now U.S. Pat. No. 5,277,820, which is hereby incorporated by reference in its entirety. Likewise, the advantageous sorbent circulation system and method described in this prior application is effective to advance sorbent suspension through hollow fiber plasmafilters and hemofilters, and is generally applicable to advance sorbent suspension through a variety of extracorporeal treatment devices having blood and sorbent sides separated by a membrane, and thus also forms a part of the applicant's invention.

The sorbent suspension used for plasmafiltration or hemofiltration in the invention can include powdered surface adsorptive agents, physiologic electrolytes and macromolecular flow inducing agents. In general, these components are present in effective amounts to achieve the desired removal of substances from and electrolyte balance in the blood of the patient while maintaining the stability and fluidity of the sorbent suspension. Because plasmafiltration membranes as used in the invention can potentially pass endotoxins, it is preferred that the sorbent suspension be free from measurable endotoxins. While general sorbent suspension production techniques have been sufficient for these purposes, if necessary, measures can be taken sanitize or sterilize the suspension, for example using heat or radiation (e.g. gamma-radiation), to assure that the sorbent suspension is substantially free from bacteria or other microbial growth which could potentially generate endotoxins or other harmful substances.

The powdered surface adsorptive agent used for plamsfiltration or hemofiltration can be any one of many known to those practiced in this area, but is preferably powdered activated charcoal. Further, the powdered surface adsorptive agent preferably has an average particle diameter of not greater than about 100 microns. More preferably, this average particle diameter is less than about 50 microns, with 90% or more of the particles having diameters not greater than about 75 microns. Particles exceeding 75 microns in diameter can be screened if necessary. Most preferably, the powdered charcoal used in plasmafiltration and hemofiltration in accordance with the invention has an average particle diameter of not greater than about 25 microns. As one example, a suitable finely powdered activated charcoal is available from American Norit Company, Inc. of Jacksonville, Fla., U.S.A., which can be screened to remove particles larger than those desired.

One preferred sorbent suspension of the invention includes only charcoal, and is free from ion-exchangers or macromolecular flow inducing agents. However, macromolecular flow inducing agents, when used, function to maintain the stability of the sorbent suspension formulation (i.e. helps to prevent solids from settling out of suspension) and maintain the flow properties of the suspension. One desirable flow inducing agent is a nonionic, hydroxyl-containing polymer such as a glycol derivative. Suitable agents of this type are available from BASF Wyandotte of Parsippany, N.J., U.S.A. under the trademark "Pluronic" polyols. These Pluronic polyols are polyoxyalkylene derivatives of propylene glycol. To date, applicant has used Pluronic F68, which functions both as a flow inducing agent and a defoaming agent. Another flow agent that has been included in preferred suspensions is macroreticular polyvinylpyrrolidone.

The types and amounts of electrolytes included in the suspension formulation will depend upon the specific needs of the patient and will be readily determinable by physicians or others skilled in the area. Typically, the electrolytes will include sodium and chloride (e.g. optionally provided as sodium chloride), and can also include bicarbonate, potassium, calcium, or any other electrolytes to be regulated in the patient. As indicated, however, the types and amounts of electrolytes may vary widely depending on patient needs.

The sorbent suspension formulation may also include an ion-exchanger to bind ionic chemicals, e.g. ammonium, etc., which may occur in the patient's blood. Many suitable ion exchangers including both resins and other materials such as zeolites are known in the art. When included, the ion-exchanger is preferably a cation-exchange resin, which is desirably loaded with sodium or calcium. For example, to date, sodium polystyrene sulfonate has been a preferred material.

The surface adsorptive agent, electrolytes, flow inducing agents and any other additives will usually comprise about 5% to 30% by weight of the sorbent suspension formulation as a whole, with the remainder being water. Typically, solid sorbents will comprise about 2% to 25% by weight of the suspension formulation, and electrolytes will comprise about about 1% to 5% of the suspension formulation. Within these parameters, more preferred sorbent suspension formulations comprise about 2% to 20% powdered surface adsorptive agent, up to about 10% ion-exchanger, and up to about 1% flow agent such as a polyol and/or polyvinylpyrrolidone.

The sorbent suspension can also include viable hepatic cells, e.g. xenogenic or allogenic cells, alone or in combination with one or more of the solid adsorbents and other materials described above, to assist in the effective removal of toxins. For example, hepatocytes can be isolated from suitable donor tissue, purified and microencapsulated in polymer as described by Dixit et al., *Hepatology* 1990:12:1342. These microencapsulated cells can then be used directly in the sorbent suspension, or can be cryopreserved until use, for example as described by Dixit et al., *Transplantation* 1993; 55:616–22. When hepatic cells are so used, plasma is effectively separated from the blood by passage through the plasmafilter membrane, and proteins and toxins are convected into contact with the cells circulating exterior of the membrane. After the cells have acted upon the toxins, the plasma is returned through the membrane and back into the patient.

In connection with plasmafiltration or hemofiltration devices and methods, there are many suitable hollow fiber membranes which are known for use in plasmafiltration or hemofiltration of blood, and those skilled in the area will be readily able to select and utilize a suitable membranes in the present invention. Such membranes can be, for example, cellulosic membranes (e.g. cellulose acetates), and will have pore sizes sufficiently large to allow passage of plasma proteins (e.g. in plasmafiltration) and/or middle molecular weight blood toxins (e.g. in hemofiltration), suitably having molecular weight cutoffs of about 50,000 or above, e.g. 50,000 to 6,000,000. Suitable plasmafiltration and hemofiltration membranes include, for example, those known under the designations F-80 (50,000 m.w. cutoff, Fresenius USA, Inc., Walnut Creek, Calif.), Altrex 140 (70,000 m.w. cutoff, Althin Medical, Inc., Miami Lakes, Fla.)), CT190G (60,000 m.w. cutoff, Baxter, Deerfield, Ill.), and Plasmaflo AP-05H (L) (about 1,000,000 m.w. cutoff, Asahi Medical Co., Ltd., Tokyo, Japan). More preferred plasmafiltration or hemofiltration membranes will have pore sizes which transmit albumin or middle molecular weight molecules with selectivity over larger molecules, and thus will provide removal of toxins while minimizing potential interference with other blood functions. For example, the Plasmaflow AP-05H(L) plasma separator (0.5 square meters) has about a 5% rejection of albumin during unidirectional filtration, but about an 80% rejection of macroglobulins.

In connection with dialysis when used in the present invention, there are many dialyzer membranes which are known for use in dialyzing body fluids such as blood, and those skilled in the area will be readily able to select and utilize a suitable membranes in the present invention. One suitable membrane is a cellulosic membrane, particularly one composed of regenerated cuproammonium cellulose (Cuprophan).

In circumstances where only plasmafiltration or hemofiltration (and not dialysis) of the blood or other fluid is desired, the membrane in the dialysis instrument need not be a dialysis membrane, and thus may be one which is impermeable to blood and its components, e.g. a membrane formed from a suitable compliant plastic film. Moreover, where only plasmafiltration or hemofiltration is desired, the dialysis instrument need not be employed at all, and any means of circulating the sorbent suspension against the exterior of the hollow fiber membranes while passing the blood or other fluid through the interior of the membranes (with bidirectional flow of the blood or fluid across the membranes) will be suitable. For example, the hollow fiber membrane cartridge could have sorbent side connections to a container filled with sorbent suspension. While the sorbent suspension is circulated through the cartridge, for example by a roller pump, the pressure changes in the blood side (created automatically by roller pumps) would create the desired bidirectional flow of plasma or other fluid across the membranes. Such systems will provide high clearance of protein-bound or middle molecular weight toxins with great simplicity and low cost.

The inventive plasmafiltration or hemofiltration methods of the invention are advantageously performed in connection with a preferred, dialysis instrument including a parallel plate dialyzer and moving the sorbent suspension formulation in a counter-current mode by the direct application of alternating negative pressure and positive pressure on the dialysate side, as described in more detail in Examples 1 and 2 below. The preferred system also creates a slight back and forth motion of the sorbent suspension formulation, which agitates, locally mixes, and helps to prevent settling of the suspension.

In another embodiment, illustrated in FIG. 7 and discussed more particularly below in connection with Example 4 below, separate bags of sorbent are used for a dialysis instrument (a parallel plate dialyzer, PPD) and a hollow fiber device (HFD) connected in series. The use of a separate HFD sorbent bag allows for limiting plasma loss, separate measurement of the volume of the sorbent bag (by a scale), and measurement of the amount of plasma returned to the patient at the end of the treatment, in addition to other advantages. A separate, advantageous pumping mechanism based on a bidirectional roller pump is also used for the HFD sorbent. On the blood side, an expansion chamber draws a predetermined amount of plasma from the sorbent suspension to the blood side during each blood inflow cycle, then expels blood and plasma downstream during blood outflow. This expansion chamber provides a volume and pressure limited pressure limited pumping action. In addition, a unidirectonal flow through the HFD sorbent reservoir (bag) is created in this improved system, to minimize settling in the bag and to minimize recirculation of recently filtered plasma going back into the HFD. The system of FIG. 7 also provides for the use of a sorbent containing essentially no solids other than charcoal (preferably having an average diameter of about 25 microns or less), which has been found to help prevent undesired clogging of the system. The preferred system (FIG. 7) also provides countercurrent sorbent flow, which is expected to lead to slightly less recirculation of plasma than with the system of FIG. 5. Additional details and advantages of the preferred system are discussed in Example 4 below.

Extracorporeal blood treatments of the invention can be used to safely and effectively treat the coma and illness of hepatic failure and to improve a patient's clinical condition as evidenced by improved physiologic and neurologic patient status. Methods of this invention can also be successfully used in treating drug overdose, even with highly-protein-bound drugs (i.e. drugs which are 75% or more protein bound). It is also expected that methods and devices of the invention will be effective in treating patients with renal failure, uremia, or other conditions benefited by removal of toxins from the blood. Further, plasmafiltration and/or dialysis methods of the invention can be used in hemofiltration to treat and remove toxins from the hemofiltration ultrafiltrate, and return the treated ultrafiltrate to blood. In this manner, the use of large volumes of sterile replacement fluid can be ameliorated or eliminated.

The invention will now be described with reference to the following specific Examples which are illustrative, and not limiting, of the invention.

EXAMPLE 1

Operation and Components of Preferred Vacuum/Pressure Operated Flow-Through Dialysis System FIG. 1 is a perspective view of a preferred dialysis system 11 sitting on a standard hospital cart, which can be used in methods of the invention. Generally, the preferred dialysis system 11 is similar in some respects to the dialysis instrument disclosed in my earlier U.S. Pat. No. 4,661,246 issued Apr. 28, 1987, which is hereby incorporated herein by reference in its entirety. However, to fill and empty the dialyzer of blood, the present system uses the direct application of pressure and vacuum to give positive and negative pressure changes in the dialysate. This increases the blood flow and enhances the mixing of the sorbent suspension formulation, as well as helps to maintain optimal chemical gradients across the dialysis membrane.

Figure 2:
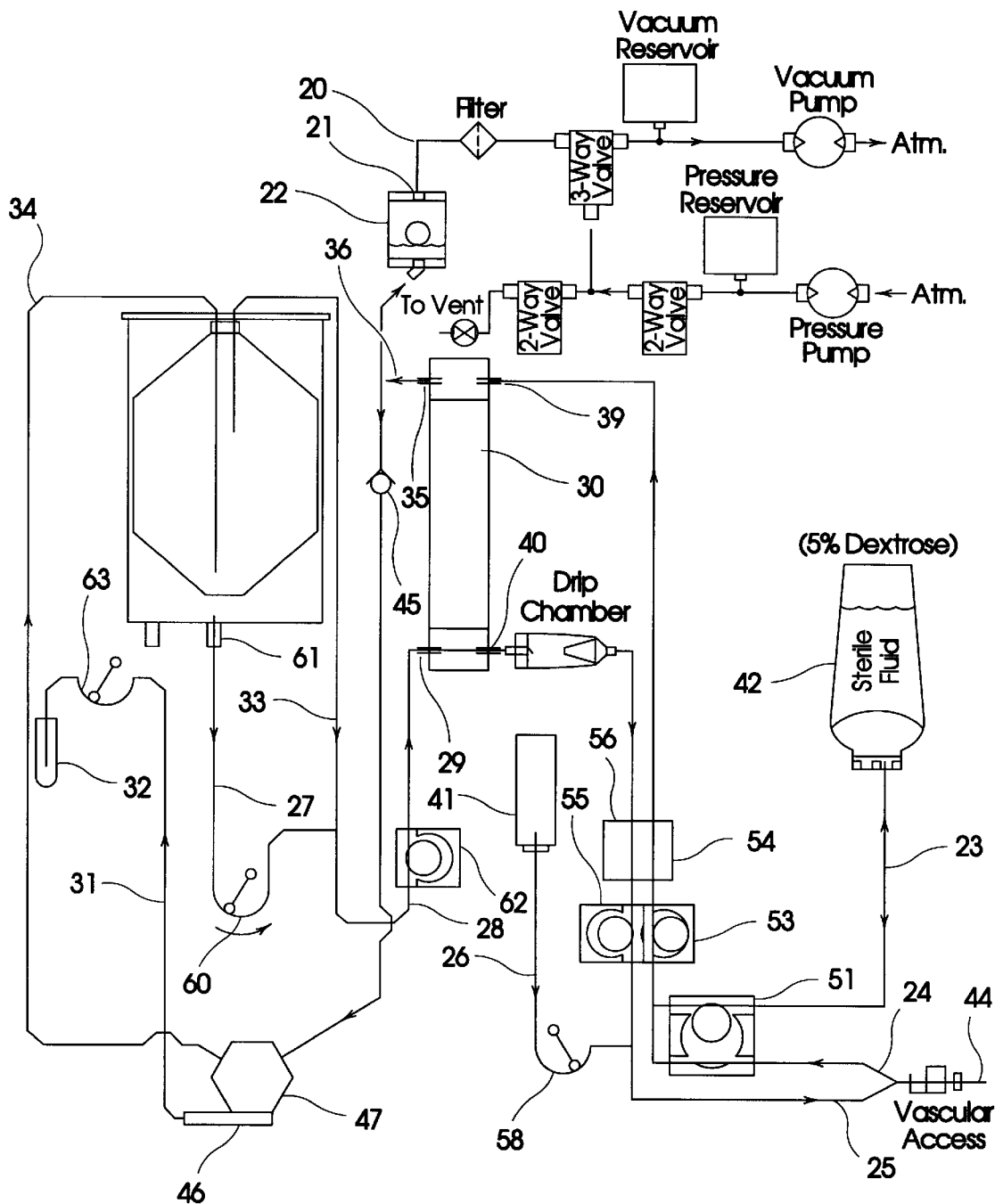
FIG. 2 is a schematic representation of the hydraulic system of the dialysis system of FIG. 1.

With continued reference to FIG. 1, the dialysis system 11 includes a machine base 12, reservoir tank 13 with cover 14, a sorbent bag 15 containing sorbent suspension materials, disposable pack 16 (including the plate dialyzer), and power supply 17 (providing vacuum, pressure, and DC power to the machine base). Referring now also to FIGS. 2 and 3, FIG. 2 is a hydraulic schematic of the dialysis system, and FIG. 3 provides in parts A and B a summary of the mechanics and hydraulics of operation of the system during blood inflow and outflow, respectively. Generally, in the following discussion, the numbers 20–47 will be used to designate components on the disposable pack 16, whereas numbers 50 and above will designate components of the machine base 12. In FIG. 1, the machine base 12 and disposable pack 16 are shown separated. Of course, in use together, the pack 16 is mounted to machine base 12 and their respective components assembled generally as follows.

Vacuum/pressure line 20 from top port 21 of accumulator 22 is connected to vacuum pressure port 50 on machine base 12 which feeds vacuum and pressure from the respective sources thereof in power supply 17. Prime tube 23 is seated into the upper side of prime/rinse clamp 51 and through prime fluid sensor 52. The blood inflow tube 24 is seated into the lower side of prime rinse clamp 51, blood inflow clamp 53 and the blood inflow sensor 54. The blood outflow tube 25 is seated into blood outflow clamp 55 and blood outflow sensor 56, and fluid level sensor 57 is placed onto accumulator 22. Reinfusate tube 26 is loaded into reinfusate pump 58 and reinfusate fluid sensor 59. Dialysate tube 27 (prior to the "Y" split) is loaded into dialysate pump 60 and its end connected to water port 61. Branch of dialysate tube 28 (after the "Y" split) which connects to the dialysate inlet 29 of dialyzer 30 is seated into dialysate-in clamp 62. Filtrate line 31 is loaded into filtrate pump 63 and into filtrate fluid sensor 64. Filtrate line 31 is also connected to filtrate disposal bag 32 which is vented. Three liters of sterile water are added to reservoir tank 13. Sorbent bag 15 is suspended from reservoir cover 14. Tubes 33 (leading to dialysate inlet 29) and 34 (leading to the exit port of accumulator 23 and also connected to dialysate outlet 35 via line 36) are connected to lines 37 and 38 provided on and leading into sorbent bag 15.

The following steps are conducted under sterile conditions. Blood inflow line 24 and blood outflow line 25 are connected to blood inlet 39 and blood outlet 40 of dialyzer 30, respectively. Reinfusate solution (e.g. $CaCl_2$ solution and appropriate amounts of KCl and/or NaCl solution) is injected into reinfusate bag 41. Reinfusate line 26 is connected to reinfusate bag 41 and a drip chamber in the line is partially filled. Prime tube 23 is connected to prime bottle 42 containing priming fluid, e.g. 5% dextrose. If desired, replacement fluid can be provided via fluid replacement line 43.

Thus, after the above assembly, the blood inflow 24 and blood outflow 25 tubes pass from a single access line 44 through clamps 53 and 55 and optical monitors 54 and 56 to connect to the top 39 and bottom 40 openings of the blood side of the dialyzer 30. Cylindrical accumulator 22 attaches to the dialysate space at the top opening 35 of the dialysate side of dialyzer 30, and alternating strong vacuum (i.e. negative pressure) and modest positive pressure in accumulator 22 (provided by line 20 through port 21 above the fluid level) alternately draws dialysate into and expels dialysate from accumulator 22, which expands and compresses the membranes of dialyzer 30 (as illustrate by the arrows, FIG. 5), while the automatically controlled blood inflow and outflow clamps 53 and 55 assure that blood passes unidirectionally through the dialyzer 30, at an average rate of up to 250 ml/min (in 5 cycles). The ratio of inflow/outflow cycle times determines the ultrafiltration rate, from a minimum of about 200 ml/hr at a ratio of about 1.45, to about 600 ml/hr at a ratio of 2.45.

In the preferred dialysis system 11 utilized in the specific Examples, the dialyzer was a 1.6 $m^2$ COBE parallel screen-plate dialyzer having dialysis membranes composed of regenerated cuproammonium cellulose (Cuprophan) and having a functional molecular weight cut-off of about 3000 daltons, i.e. only molecules of about 3000 daltons or less will pass through the membrane.

As opposed to many previously-known dialysis systems, the system used in the invention contains a sorbent suspension in the dialysate instead of merely a dialysis solution. Flow of the suspension is generally counter-current, and is both bidirectional between the accumulator 22 and dialyzer 30, and circular between the dialyzer 30 and sorbent reservoir 15.

In summary, during the first part of blood inflow (see particularly FIG. 3A), clamp 62 on the dialysate inflow line 33 opens, allowing sorbent suspension to flow from the sorbent reservoir 15 through the entire dialyzer 30, filling the accumulator 22 to the level of sensor 57. Clamp 62 then closes and remains closed during the remainder of inflow and all of outflow (see particularly FIG. 3B), when pressure in the accumulator 22 returns some suspension to the dialyzer 30 and passes some through one-way valve 45 to return to the reservoir 15 via dialysate return line 34. In typical operation, each minute, about 900 ml of sorbent suspension flows into accumulator 30 (in 5 cycles). 600 ml of sorbent suspension flows back into the dialyzer 30, and 300 ml flows from the accumulator 22 into the sorbent reservoir 15. This, along with the expansion and contraction of the dialyzer membranes, keeps the sorbent suspension well mixed at the dialyzer membrane surface. Typical blood side and dialysate side pressure, and the blood volume of the dialyzer over time during such operation are shown in FIG. 4. As can be seen, both the blood side and dialysate side pressures alternate between positive and negative pressure, while the spring action of the plate dialyzer membranes ensures that there is constantly a positive pressure gradient from blood side to dialysate side.

In one suitable system, sorbent bag 15 initially contains dry sorbent materials to which the system automatically adds 1.5 liters of sterile water from reservoir tank 13 via port 61 during priming. This operation is powered by dialysate pump 60. For the Examples given below, the sorbent materials in bag 15 were as follows:

140 grams powdered activated charcoal (300,000 square meters surface area, between 5 and 53 micron mean particle diameter, 70 micron maximum particle diameter)

80 grams cation exchanger (sodium polystyrene sulfonate, PSS, functional binding of 80 mEq).

1.5 grams Pluronic F68.

3.0 grams polyvinylpyrrolidone (PVP).

sodium bicarbonate and sodium chloride to result in physiologic starting concentrations in the dialysate sorbent suspension after priming (sodium=140 mEq/L, bicarbonate=35 mEq/L, chloride=105 mEq/L).

The priming fluid for the blood side of the dialysis system was one liter of 5% dextrose from container 42 attached to blood inflow tube 24 via tube 23. During priming, priming/rinse clamp automatically opens prime tube 23 while closing blood inflow tube 24. Priming fluid is thus pulled into the system rather than blood. Glucose passes across the membranes of the dialyzer 30, and 20 grams binds to the charcoal, while sodium chloride, and bicarbonate pass from the suspension into the priming fluid. During dialysis, glucose disassociates from the charcoal and returns to the patient (unless the patient's glucose is very high). A reinfusate of sterile calcium chloride and potassium chloride was pumped by reinfusate pump 58 from reinfusate container 41 through tube 26 into the outflow line 25 at a diminishing rate throughout the treatment, to offset removal by the cation exchanger.

The system also includes a variety of sensors to make operation safe, simple and highly automated, including:

a scale to weigh the entire top of the machine, to measure volumes ultrafiltered from and returned to the patient;

blood sensors (54 and 56) to measure foam, bubbles, particles of blood in the inflow and outflow lines 24 and 25, and to measure flow rate on the inflow line 24;

hemoglobin sensor 46 to chemically detect hemoglobin within the sorbent suspension if there is a membrane blood leak. For this function, a filtrate collector 47 provides a solid-free sample of the dialysate fluid to hemoglobin sensor tape which changes color if hemoglobin is present. The tape is automatically wetted with samples of dialysate, advanced and monitored for color change by a reflectometer. The wetting of the tape is controlled by filtrate pump 63 which further pumps excess filtrate via tube 31 into collection container 32.

empty line sensors on all fluid-filled lines;

temperature sensor for fluid in the reservoir tank 13 surrounding the sorbent bag 15 (optimally heated to about 37° to 40° C. by heating elements also provided in the machine).

The computers of the system automate many of the steps of treatment, including:

priming of the machine, observing lines to determine that all air is removed;

returning fluid to the patient when desired final weight is obtained or on command (for the latter, automatically adjusting ultrafiltration to reach desired final weight).

rinsing the dialyzer and blood lines at the end of treatment; and recording, storing and transferring data concerning progress of each treatment.

EXAMPLE 2

COMBINED DIALYSIS/PLASMAFILTER or HEMOFILTER DEVICE

FIG. 4 provides a schematic diagram showing the hydraulics of a combined dialysis/plasmafilter device in accordance with the invention. As shown, the device incorporates a parallel plate dialyzer ("PPD") connected in series with a hollow fiber membrane device ("HFD"). In this regard, it will be understood that the present invention is not limited to such a combined device, and that the HFD could be used as the sole agent for treatment of the blood. Further, when used in combination with the PPD, the HFD can be incorporated in any suitable location within the sorbent circulation side of the PPD. Preferably, the HFD will be incorporated to as to achieve high bidirectional plasma flow across the membranes of the HFD, with a net flow of about zero to prevent increasing sorbent volume (which would increase the volume of distribution for albumin and increase loss of albumin from the patient). The HFD is also desirably incorporated so as to provide blood treatment rates over 150 ml/min., to allow high filtration rates across the membranes and permit high clearance of protein-bound or middle molecular weight substances.

In the illustrated arrangement, the HFD is connected in series with the PPD such that sorbent suspension exiting the sorbent reservoir first passes through the PPD and then the HFD. More particularly, sorbent is first drawn from sorbent bag 101 and into sorbent inlet 102 of the PPD. Sorbent exits sorbent outlet 103 and is drawn into accumulator reservoir 104, whereafter it is expelled from accumulator reservoir 104 and passes through check valve 105. The sorbent suspension then passes into HFD inlet 106 and through the outer chamber of the HFD, thus passing into contact with exterior surfaces of the hollow fibers 107 in the HFD package. Sorbent suspension exits the HFD from outlet 108, and passes through blood leak detector 109 and back into sorbent bag 101. The PPD can be suitably operated as described in Example 1 above. In this manner, the sorbent suspension is also effectively agitated and mixed at the surface of the membranes in the HFD. Additionally, when alternating positive and negative pressure is applied to the sorbent circuit via the accumulator reservoir 104, check valve 105 prevents negative pressure from being applied to the HFD sorbent side, and creates only intermittent positive pressure (FIG. 5(b)). In this system, the blood-side (see FIG. 5(a)) and dialysate-side pressures vary with each cycle, but are balanced on average, thus creating a bidirectional flow in each cycle but with zero net filtration (there is net sorbent to blood filtration in the HFD, offsetting ultrafiltration of the PPD, several hundred ml/hr.).

On the blood side, blood passes from the patient access and into blood inlet 110 of the PPD, with the intermediate addition of saline from reservoir 111. Where a dialysis membrane (as opposed to an impermeable membrane) is installed in the PPD, the blood is dialyzed in the PPD as described above. Blood then exits the PPD through outlet 112 and passes into interior channels of the hollow fibers of the HFD (commercial HFD devices have a package including a plurality of hollow fiber membranes). At this point, the alternating positive and negative pressure applied on the sorbent side causes a bidirectional flow of plasma across the hollow fiber membranes, that is, the blood plasma exits and then reenters the hollow fiber membranes. While exterior of the hemofilter or plasmafilter membranes, middle molecular weight toxins and/or plasma proteins, including proteins to which toxic substances are bound, come into contact with the sorbent suspension. The toxic substances are adsorbed to the adsorbents, and in the case of plasmafiltration, the proteins, now free of toxins, are passed back into the hollow fiber membranes. Thus, effective plasmafiltration or hemofiltration of the blood is achieved as the blood passes through the HFD. Blood exits the HFD via outlet 113, and is returned to the patient through the patient access.

The pressures of the blood-side and sorbent-side will vary with the particular HFD devices employed. Thus, with a particular HFD device, in vitro tests can be done to measure filtration rate, and the vacuum and pressure operating the system will be adjusted to attain zero net filtration. Moreover, to optimize blood flow, adjustments to the ratio of inflow/outflow times can be made. The combined PPD/HFD system will, like the system described in Example 1, measure the rate of ultrafiltration by weighing the entire top of the device, including the sorbent bag. But, since the goal is net ultrafiltration of about zero, there is no need for the long inflow times of the system of Example 1. Better blood flow will be obtained using approximately equal inflow and outflow times. During in vitro tests, for example with pig blood, the driving pressures can be adjusted as above, and the net blood flow determined (by change of weight of the 3 liter container during each cycle). The inflow-outflow times can then be adjusted to give maximum blood flow. Preferably, the 200–225 ml/min average blood flow of the system of Example 1 is maintained.

EXAMPLE 3

BLOOD TREATMENT WITH DIALYSIS/ PLASMAFILTER OR HEMOFILTER DEVICE

Figure 6A:
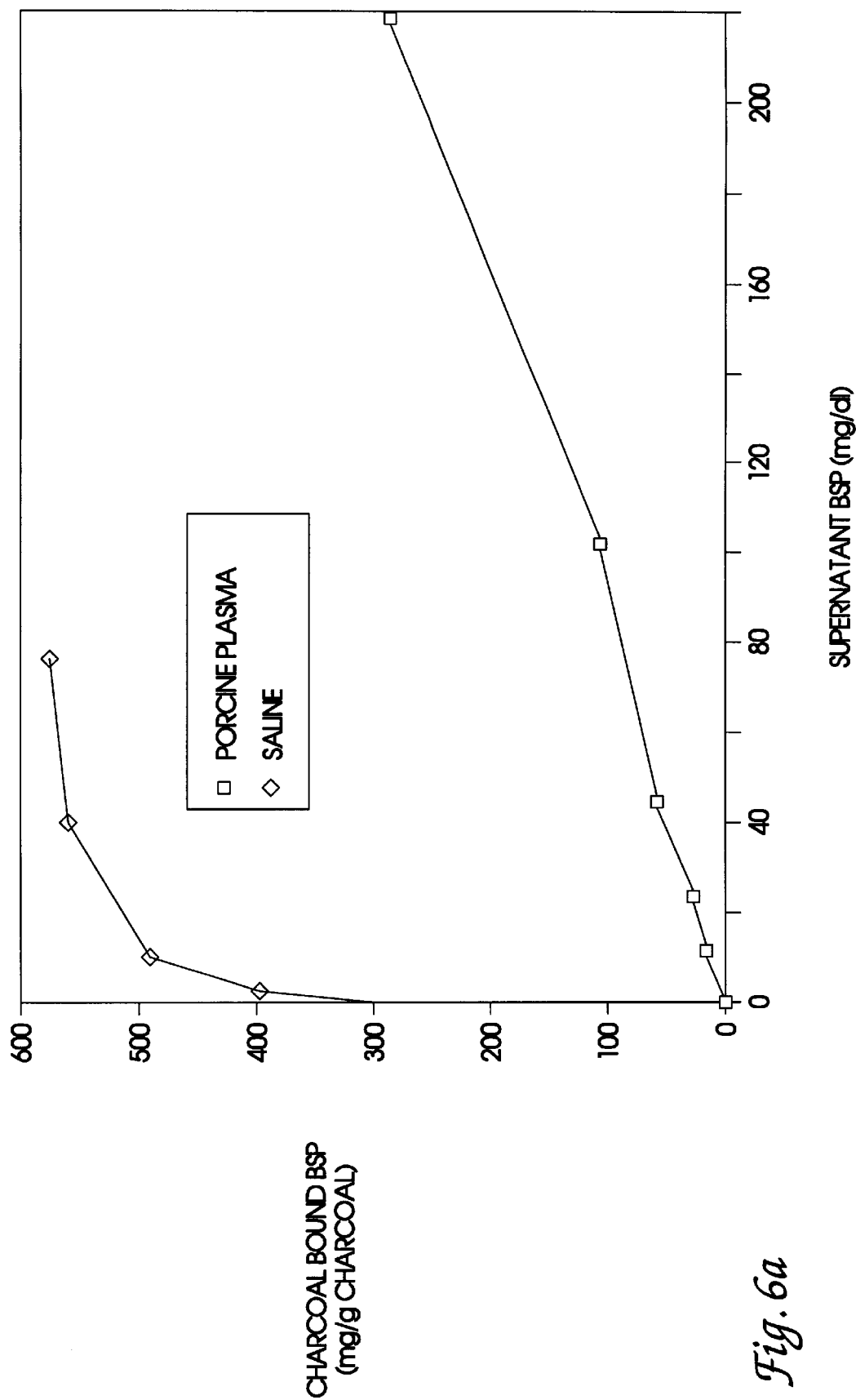
FIG. 6(a) shows a Langmuir isotherm for binding of bromsulphthalein (BSP) from saline (top line) and from porcine plasma (bottom line) to which it was first bound to charcoal.
Figure 6B:
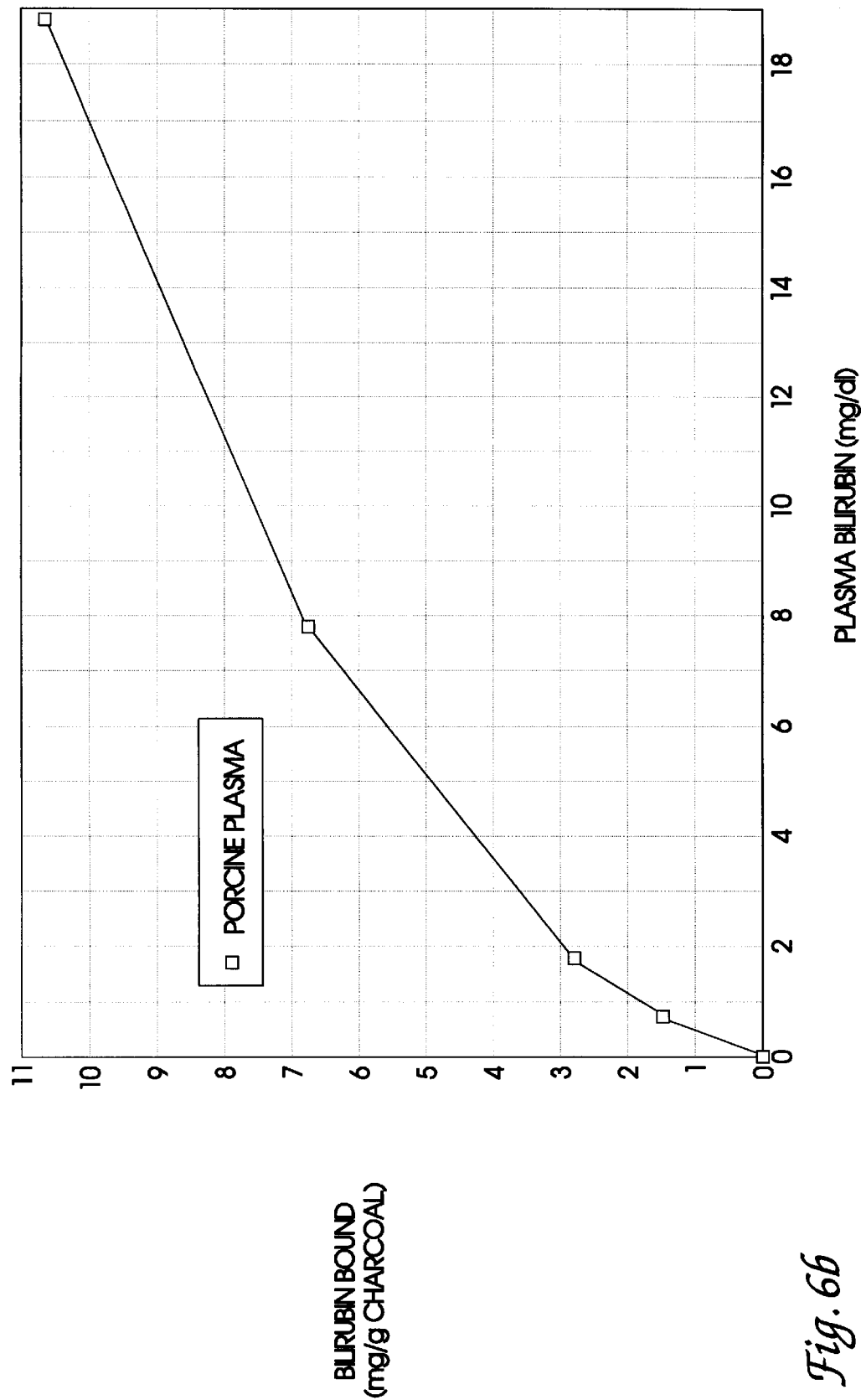
FIG. 6(b) shows a Langmuir isotherm for binding of unconjugated bilirubin from porcine plasma to which it was first bound to charcoal.

Charcoal has the capacity to very effectively adsorb middle molecular weight molecules and protein-bound toxins (see, e.g., FIGS. 6(a) and 6(b) which provide Langmuir isotherms of the adsorption of BSP from plasma and saline and of bilirubin from plasma). In the following studies, the PPD/HFD device described in Example 2 was used to determine clearance rates of some protein-bound and middle molecular weight substances from blood. 3 liters of fresh pig blood were spiked with various substances (Shown in Table 1 below), and the blood was treated using the PPD/HFD device. During several hours of treatment, the blood was continuously infused with the substances at a rate designed to maintain a constant concentration (calculated by the predicted clearance of the system). The clearances were then determined by dividing the rate of infusion by the steady-state concentration of the substance. If the blood volume changed, then the change was included in the calculation of clearance. The results are shown in Table 1, in which "Creat"=creatinine, "Bili"=bilirubin, BSP, and "Vanco"=vancomycin. Among these, creatinine is a small, non-protein bound substance, bilirubin, Elavil and BSP are small, highly protein-bound molecules, and vancomycin is a middle molecular weight, non-protein bound substance.

TABLE 1

BLOOD FLOW AND CLEARANCES (ml/min)

| Membrane | Ave Ob. | Creat | Bili | BSP | Elavil | Vanco |
|---|---|---|---|---|---|---|
| PPD only | 200 | 140 | 0 | 0 | 12 | 0 |
| F-80 | 150 | 130 | 12 | n/a | 40 | — |
| Altrex 140 (70 K) | 180 | 130 | 5 | n/a | — | — |
| Althin* | 140 | 90 | 5 | n/a | 19 | 37 |
| CT190G | 160 | 85 | 0 | — | — | 62 |
| Plasmaflo AP-05H (L) | 140 | 95 | 43 | n/a | n/a | 35 |

— (dash) = no data
n/a = data not currently available
*developmental filter from Althin Medical, Inc., m.w. cutoff = 100,000.

As can be seen, use of the HFD can provide significant increases in the clearance of middle molecular weight and protein-bound substances, and can be used in connection with the PPD to provide effective overall clearance of small and larger substances, both protein-bound and nonprotein-bound.

EXAMPLE 4

IMPROVED DIALYSIS/PLASMAFILTRATION DEVICE

Figure 7:
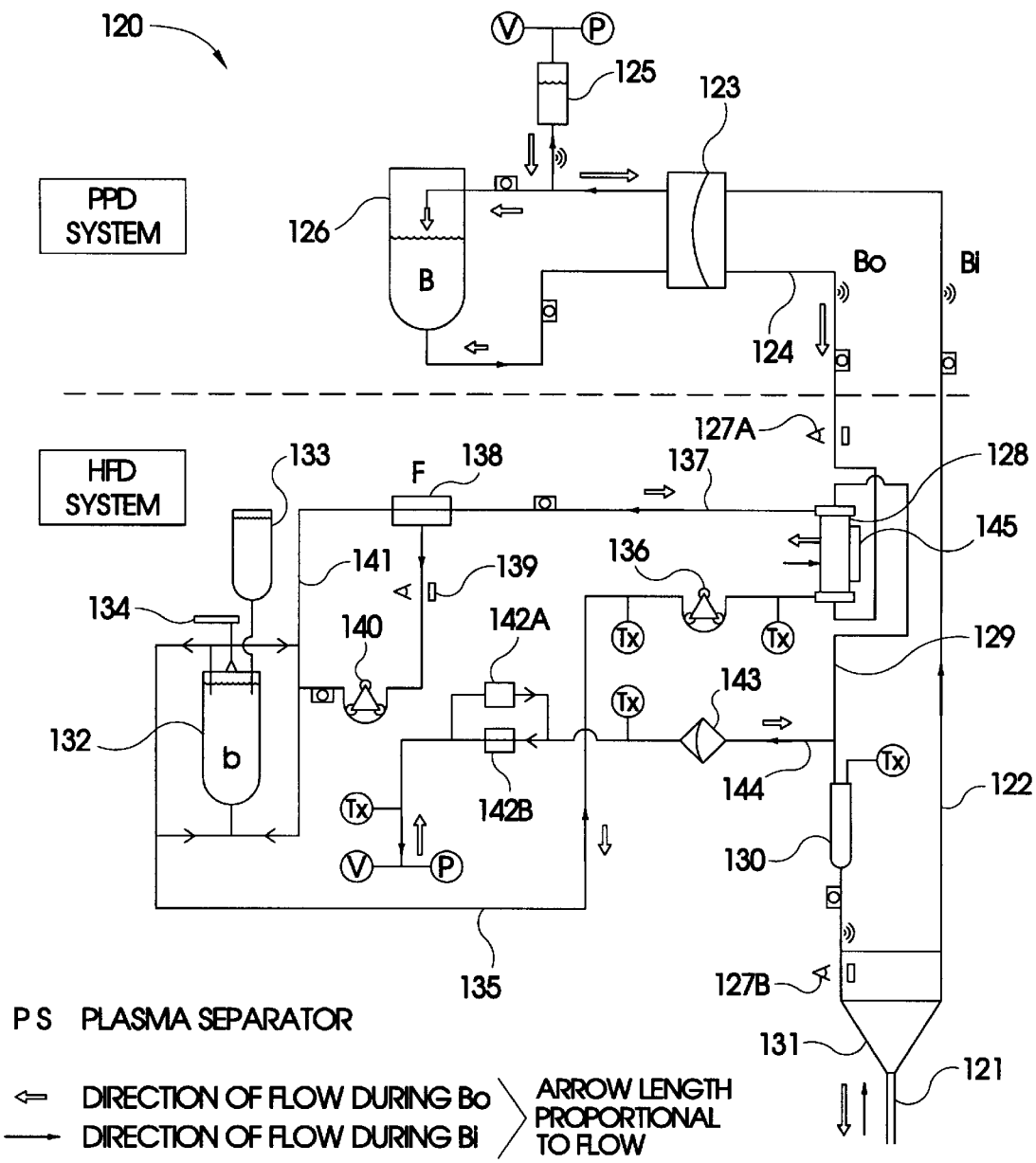
FIG. 7 shows a schematic diagram illustrating the hydraulic circuit of an improved combined device incorporating the system of FIG. 1 in series with a hollow fiber device such as a plasmafilter, in which an independent sorbent supply is used for the plasma filter.

FIG. 7 provides a schematic diagram showing the hydaulic circuit for an improved PPD/HFD system 120 in accordance with the invention. The system 120 is similar in several respects to the system of FIG. 4, and combines the functions of a PPD device such as that in FIG. 1 (represented by simplified schematic, FIG. 7, top) with a HFD device (FIG. 7, bottom). In particular, a single lumen access 121 is provided, having blood inflow line 122. Line 122 leads to the blood input side of plate dialyzer 123. Line 124 leads from the blood output side of dialyzer 123. The sorbent side of dialyzer 123 is coupled to accumulator 125, and sorbent bag 126, generally as discussed above in connection with FIG. 1.

Line 124 from the blood output side of dialyzer 123 passes through optical sensor (sorbent detector) 127, and to the blood input of the hollow fiber device 128 (plasma separator). Line 129 leads from the output of device 128 to drip chamber 130. Blood inflow line 131 leads from drip chamber 130, through optical sensor (sorbent detector) 127B, and back to single lumen access 121.

The sorbent side of the HFD system includes sorbent bag 132 which contains sorbent, and filling bag 133 for providing liquid (e.g. priming fluid) to sorbent bag 132. Scale 134 monitors the weight of sorbent bag 132.

Sorbent line 135 passes to roller pump 136, which powers the flow of sorbent through the sorbent side of hollow fiber device 128. Line 137 leads from the sorbent output of device 128 to plasma filter 138, and line 141 carries sorbent suspension from filter 138 back to sorbent bag 132. A hemoglobin detection system (for detecting blood leaks) is provided by plasma filter 138 (e.g. containing a 0.45 micron membrane), optical sensor 139 and roller pump 140. In this regard, roller pump 140 is energized to draw a sorbent free sample through filter 138 and to optical sensor 139 (e.g. detecting at 583 nm). After optical sensor, the sample will be returns to sorbent line 141 as illustrated. Hemolysis of blood within the sorbent and by the membrane of filter 138 releases hemoglobin which is measured by the optical sensor 139. In the preferred device the detection of hemoglobin indicative of a blood leak will trigger and audible alarm, stop operation of the system, and clamp all lines. Other means for drawing a sample through plasma filter 138 are also contemplated as being acceptable. For example, instead of using roller pump 140, the line containing optical sensor 139 can be coupled to a vaccuum/pressure source (e.g. "V" and "P" of FIG. 7) via an expansion chamber containing a non-gas-permeable compliant membrane dividing the chamber into blood and gas sides, and acting as a pump. The gas side of the chamber can be conncected to the vaccuum/pressure side of the chamber, so as to alternately draw sample through filter 138 and sensor 139 (upon application of vaccuum) and expel the sample back through filter 138 and into sorbent line 141 (upon the application of pressure. In such a configuration, an air filter can be installed as appropriate to prevent the passage of gas to the sorbent.

In system 120, a vaccuum/pressure source (e.g. that used for the PPD system) provides vaccuum and pressure to vacuum regulator 142A and pressure regulator 142B, respectively. These, in turn, transmit the vaccuum and pressure to expansion chamber 143, which is connected to line 129 at a position intermediate drip chamber 130 and hollow fiber device 128. Expansion chamber 143 includes a flexible membrane dividing the chamber into gas and blood sides, with the gas side connected to the vaccuum/pressure source and the blood side connected to line 129 via line 144. For example, expansion chamber 143 can be constructed from a 20 ml capacity transducer protector with a flexible membrane (normally used as a pressure-transducer protector). The pressure changes applied to the gas side of the chamber 143 cause it to function as a constant pressure pump, with a built-in limit of 20 cc for the volume of plasma which can pass through the membranes of the hollow fiber device 128 during each cycle.

The preferred system 120 also includes a vibrator device 145, e.g. a motor-driven vibrator, operably associated with hollow fiber device 128, so as to vibrate or shake device 128 during operation of system 120. It has been found that the association of such a vibrator device 145 with hollow fiber device 128 provides dramatically improved mixing of the sorbent suspension, and leads to surprisingly high increases in the clearance of molecules such as bilirubin.

The overall function of system 120 will now be more particularly described with continued reference to FIG. 7. Generally, the PPD and HFD systems are connected in series on the blood side. Blood flows first through the PPD portion and then the HFD portion. The PPD System portion operates as discussed above in connection with FIGS. 1 and 5. A 10-French single-lumen central venous catheter can be used for blood access 121. To create blood inflow in the PPD system, a vacuum is pulled from the sorbent bag 126 through the dialyzer 123, negative pressure expands the membranes, and blood is pulled in past the open Bi clamp. To create blood outflow, positive pressure is placed on the accumulator 125; sorbent suspension passes back to the bag 126, positive pressure compresses the membranes, and blood is returned past the open Bo clamp.

In the HFD system portion of the combined system 120, blood flowing out from the dialyzer 123 in the PPD system passes upward through the hollow fiber device 128 (e.g. containing plasma separator (PF) membranes) and through drip chamber 130 (e.g. 10 ml capacity) with a filter, on the way back to the single blood access 121. Just above the drip chamber is expansion chamber 143 constructed from a 20 ml capacity transducer protector with a flexible membrane (normally used as a pressure-transducer protector). A filtered air-line connection from the PPD system is attached to the other (gas) side of this chamber (with regulators to provide air pressure alternative between +100 mm Hg and −100 mm Hg). This change in pressure causes the expansion chamber to function as a constant pressure pump, with a built-in limit of 20 cc for the volume of plasma which can pass through PF membranes of device 128 during each cycle. A second Bo clamp below the drip chamber 130 closes whenever the Bo clamp of the PPF system closes. Blood-side pressure within the PF membranes of device 128 is 100–70 mm Hg during blood outflow and 0–50 mm Hg during blood inflow when both Bo clamps are closed and vacuum is applied to the expansion chamber. Blood-side positive pressure and a slight decrease in case pressure created by the sorbent-side roller pump (which operates counter-current during blood outflow at 50 ml/min) causes a net passage of plasma from blood to sorbent (20–27 ml) during each blood outflow cycle. During blood outflow, the positive pressure on the expansion chamber 143 empties it, adding its blood to that passing through the hollow fiber device 128. Rapid flow of sorbent through the case (sorbent side) of the hollow fiber device (400 ml/min, e.g., co-current) helps maintain pressure of the sorbent to help return plasma to the blood. The "fine tuning" of plasma passage into and out of the sorbent bag 132 is determined by the average pressure of the bag. If plasma entering the bag is greater than that leaving it, volume and pressure increase in the bag and this augments plasma return to blood (during blood inflow); if plasma entering the bag is less than that leaving it, volume and pressure decrease in the bag and this augments plasma removal from blood (during blood outflow). During a priming operation with dextrose/saline, the bag volume automatically becomes close to the stable volume of plasma in the bag during operation with blood. This prevents overfiltration of plasma in either direction during dialysis with blood in the system. In normal operation, the peak transmembrane pressure (TMP) is less than 60 mm Hg during blood outflow, and the average is about half this amount against the membrane surface, a condition which could result in hemolysis. During blood outflow, transmembrane pressures are similarly modest, to avoid excessive polarization of charcoal around the membranes. The bidirectional flow of plasma is important; red cells polarized against the inner membrane are lifted from the membrane during the next blood outflow cycle. Sorbents polarized against the outer surface of the membrane are lifted during the next inflow cycle In one illustrative use, the HFD system contains a 700 ml bag containing 700 grams of gamma-irradiated, sterile powdered charcoal (filtered to 25 microns) creating a 10% suspension by weight and 30% concentration by volume of plasma. This sorbent suspension is circulated through the sorbent side of the HFD system by roller pump 136 in a bidirectional manner, to help pull sorbent through the hollow fiber device (plasma filter) 128 slowly to augment plasma removal from blood, and push sorbent through the plasma filter flow to augment plasma return to the blood. One-way valves (arrows) near the top and bottom sorbent bag 132 assure that sorbent moving from the device 128 to the bag 132 enters the bottom of the bag 132. Sorbent moving from the bag 132 to the device 128 leaves from the top of the bag 132. The unidirectional flow of sorbent through the bag 132 and the small particle size (25 micron or less) results in a sorbent suspension with greater fluidity and less tendency to aggregate at any part of the sorbent circuit. The operation of vibrator device 145 also assists in preventing aggregation of the suspension and dramatically improves clearances.

Thus, the system operates by application of a defined pressure to the device 128. The volume of plasma transferred is passively determined by the resistance to plasma flow across the membranes of device 128. When red cells begin to polarize against the inner membrane surface (during a blood outflow cycle), flow of plasma decreases; when charcoal polarizes on the outer membrane surface (during blood inflow) the flow rate decreases automatically. Excessive polarization of red cells and sorbent is avoided by not moving a pre-determined volume of plasma across the membranes during each cycle. The result is a high bi-directional plasma flow across the membranes of device 128 during each cycle (20–27 ml/cycle) with net-zero plasma filtration between blood and the sorbent bag, and with very little hemolysis.

The combined system 120 can be operated to achieve the following performance:

blood treatment rates of approximately 200 ml/min using a single-lumen 10 French catheter (sufficient to allow 80–100 ml./min of plasma filtration across the plasma separator membranes of device 128 and high clearance of water-soluble toxins by the PPD System).

bi-directional plasma flow of plasma across the plasma separator membranes of device 128 of 80–110 ml/min (20–27 ml per cycle) when blood flow rate is 200 ml/min.

net plasma flow across the plasma membranes of zero, with a stable HFD system sorbent suspension volume of 700 ml during treatment (a larger sorbent volume would increase the volume of distribution for plasma proteins in the sorbent, and increase albumin loss from the body) and a PF sorbent charcoal concentration of 30% by volume (10% by weight).

accurate control of net ultrafiltration from the patient; the PPD system can still remove protein-free ultrafiltrate from the blood according to the patient's fluid management needs, without any dilution of sorbent suspension in the HFD system.

effective mixing of the sorbent suspension at the surface of the plasma separator membranes, perpetuating high clearance of protein-bound toxins for several hours.

bilirubin clearances from blood which are stable at greater than 10 ml/min for 5 hours of treatment, when the blood bilirubin concentration is maintained at 5–7 mg %.

As compared to a system such as that illustrated in FIG. 5, significant changes and improvements include:

1. The use of separate bags for the HFD sorbent and the PPD sorbents. The system of FIG. 5 contains only one sorbent bag. Sorbent flowed from the sorbent bag of the PPD system, through the dialyzer, through the hollow fiber device, and back to the bag. With a second, smaller HFD sorbent bag, it is possible to limit the amount of plasma loss from the patient, separately measure the volume of the sorbent bag by a scale, and measure the amount of plasma returned to the patient at the end of the treatment. Further, the PPD system can continue to remove fluid and potassium from the patient, while the HFD sorbent maintains a constant volume of plasma. In addition, some additives to the PPD sorbent suspension may create specific chemical or osmotoic effects in patients. These additives could not be used as safely or easily to the HFD sorbent portion (where sterility must be maintained).

2. Use of a separate pumping mechanism for the HFD sorbent. The use of a separate HFD sorbent bag required the use of a separate mechanism to propel sorbent through the HFD and back to the bag. In the system of FIG. 5, this function is performed by the accumulator of the PPD system, responding to air pressure changes. With such a system, sorbent flow is bidirectional (co-current with blood through the HFD towards the bag during blood outflow, but flowing back from the sorbent bag and through the membranes to the blood during blood inflow). In the system of FIG. 7, a roller pump is used, which can operate bidirectionally to maintain back-and-forth flow of sorbent through the HFD.

3. Elimination of recirculation and retreatment of plasma. In the system of FIG. 5, the plasma passing from sorbent to blood moves back towards the sorbent dialyzer, since this device is supplying negative pressure on the blood side. This means that this plasma would be the first to filter out from the blood in the HFD and interact with sorbents again. To prevent recirculation in the system of FIG. 7, a clamp is provided between the dialyzer 123 and the HFD 128, which closes synchronously with the clamp downstream of the HFD 128, during each blood inflow. The blood-side expansion chamber 143 near the HFD 128 draws 20 ml of plasma from the sorbent suspension to the blood side during each blood inflow cycle, then expels blood and plasma downstream during blood outflow. This chamber provides a volume limited and pressure limited pump (e.g. with pressure regulated at +200 mm Hg and vacuum at −50 mm Hg).

4. Unidirectonal flow through the HFD sorbent bag 132. Though the roller pump 136 of the HFD sorbent circuit operates bidirectionally, unidirectional blood flow through the sorbent bag is preferred, to minimize settling in the bag and to minimize recirculation of recently filtered plasma going back into the HFD 128. Four one-way valves (indicated by arrows) are placed on the tubes leading the bag 132, to assure that flow through either tube towards the bag entered the bottom of the bag, and flow from the bag left the top. In an illustrative system, flow from bottom to top of the bag averages 225 ml/min (alternating between 400 ml/min and 50 ml/min during each half cycle). However, since most plasma passing out of the HFD plasma filter membranes passes back into the membranes during each half cycle, the net transfer of plasma into the HFD sorbent circuit (containing roller pump, tubing, and sorbent bag) is only 25 ml/min.

5. Single component sorbent. The tests of the system illustrated in connection with FIG. 5 included the PPD sorbent. This sorbent contains powdered charcoal, IRP-69 cation exchanger, and flow-inducing agents. Using a sorbent containing only charcoal (free from cation exchanger and flow-inducting agents helps to prevent undesired clogging of the system.

6. Countercurrent sorbent flow. In the system illustrated in FIG. 5, co-current flow of sorbent and blood occurred when flow was rapid (during blood outflow). In the preferred system illustrated in FIG. 7, the general flow of sorbent is opposite the blood flow, which is expected to lead to slightly less recirculation of plasma than with the system of FIG. 5.

7. Small particle size charcoal. The powdered charcoal used in the system of FIG. 5 was screened to be less than 75 micron. Minimum charcoal particle size is 1 micron. To minimize clogging around the membranes of the HFD device, it is preferred to screen the sorbent to 25 micron maximum particle size. This helps to stabilize bidirectional plasma flow.

8. Varying cycle time to increase and decrease PH sorbent bag volume. To increase net transfer of plasma between the bag and the blood, it is preferred to alter the volume of the sorbent bag 132, e.g. by approximately 100 ml, each 15 minutes. This can be accomplished for example by changing the inflow/outflow cycle time from 7 seconds/5 seconds to 5 seconds/7 seconds each 15 minutes. The 7/5 cycle time can be implemented at 5 hours of treatment to dehydrate the HFD sorbent bag 132 and decrease the volume of plasma in the bag by over 50% by the end of treatment at 6 hours.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A filtration process for removing blood toxins, comprising:

passing a fluid containing protein bound and/or middle molecular weight blood toxins through the interior of a hollow fiber membrane;

during said passage of fluid, circulating a sorbent suspension against exterior surfaces of the hollow fiber membrane;

during said passage of fluid and circulation of sorbent suspension, periodically creating pressure differentials across the hollow fiber membrane so as to cause the fluid or a fraction thereof to alternately exit and re-enter the interior of the hollow fiber membrane in a bidirectional flow pattern across the hollow fiber membrane, wherein said exiting fluid or fraction contains the protein bound and/or middle molecular weight toxins which contact said sorbent suspension so as to effectuate removal of said toxins from said fluid.

2. The process of claim 1, and also including vibrating said hollow fiber membrane so as to increase the mixing of the sorbent suspension as it is circulated.

3. The process of claim 2, wherein said hollow fiber membrane is a plasmafiltration membrane, whereby middle molecular weight toxins and protein-bound toxins are removed from said fluid.

4. The process of claim 1, wherein said fluid is blood.

5. The process of claim 1, wherein the fluid contains red blood cells, and wherein the red blood cells are polarized against the hollow fiber membrane during a first flow direction of the bidirectional flow pattern in which the fluid or fraction thereof exits the hollow fiber membrane, and the polarized red blood cells are lifted from the hollow fiber membrane during a second flow direction of the bidirectional flow pattern in which the fluid or fraction thereof re-enters the hollow fiber membrane.

6. A blood treatment device which comprises:
   a hollow fiber membrane;
   a pump fluidly connected to the interior of said hollow fiber membrane and adapted to pass a fluid containing middle molecular weight and/or protein-bound blood toxins through the interior of said hollow fiber membrane;
   a chamber surrounding said hollow fiber membrane, said chamber further being fluidly connected to a supply of a first sorbent suspension;
   a pump adapted to circulate said first sorbent suspension through said chamber and against exterior surfaces of said hollow fiber membrane; and
   an apparatus for vibrating said chamber to increase mixing of the sorbent suspension as it is circulated in the chamber against exterior surfaces of the hollow fiber membrane.

7. The device of claim 6, and also including means for causing said fluid or fractions thereof passing through the interior of the hollow fiber membrane to alternately exit and re-enter said interior.

8. The device of claim 7, wherein said hollow fiber membrane is a plasmafiltration membrane, said means for causing includes a pump, and said apparatus for vibrating includes a motor-driven vibrator.

9. The device of claim 7, further comprising a dialysis instrument adapted to dialyze said fluid fluidly connected in series with the interior of said hollow fiber membrane, upstream of the interior of said hollow fiber membrane.

10. The device of claim 9 wherein said dialysis instrument includes a plate dialyzer having a blood side and a sorbent side, and a second sorbent suspension circulated on the blood side of the plate dialyzer.

11. The device of claim 10, wherein said first and second sorbent suspensions are provided from separate sources.

12. The device of claim 11, wherein the pump adapted to circulate the first sorbent suspension is a roller pump.

13. The device of claim 12, wherein the first sorbent suspension is circulated counter-current to the fluid in the hollow fiber membrane.

14. A method for circulating a sorbent suspension in a device for extracorporeal treatment of blood or a blood fraction, said method comprising the steps of:
   providing said device having a sorbent circulation circuit and a blood circulation circuit separated by membranes, said membranes being compliantly formed to expand and contract in response to alternating positive pressure and negative pressure applied to said sorbent circulation circuit and thereby advance a sorbent suspension through said sorbent suspension circulation circuit;
   providing an accumulator reservoir fluidly connected to said sorbent circulation circuit and operable to alternately accumulate and expel sorbent suspension in response to alternating negative pressure and positive pressure applied to said accumulator reservoir, said accumulator reservoir thereby communicating said alternating negative and positive pressure to said sorbent circulation circuit;
   applying alternating positive pressure and negative pressure to said accumulator reservoir so as to communicate the same to said sorbent circulation circuit and cause said compliant membranes to expand and contract, whereby said sorbent suspension is advanced through said sorbent suspension circuit.

15. The method of claim 14, wherein said membranes are dialysis membranes.

16. A device for extracorporeal treatment of blood or a blood fraction, which comprises:
   a sorbent circulation circuit and a blood circulation circuit separated by membranes, said membranes being compliantly formed to expand and contract in response to alternating positive pressure and negative pressure applied to said sorbent circulation circuit and thereby advance a sorbent suspension through said sorbent suspension circulation circuit;
   an accumulator reservoir fluidly connected to said sorbent circulation circuit and operable to alternately accumulate and expel sorbent suspension in response to alternating negative pressure and positive pressure applied to said accumulator reservoir, said accumulator reservoir thereby communicating said alternating negative and positive pressure to said sorbent circulation circuit;
   a source of positive pressure and of negative pressure fluidly connected to said accumulator reservoir wherein when alternating positive pressure and negative pressure are alternately applied to said accumulator reservoir, the same is communicated to said sorbent circulation circuit to cause said compliant membranes to expand and contract, whereby said sorbent suspension is advanced through said sorbent suspension circuit.

17. The device of claim 16, wherein said membranes are dialysis membranes.

18. A filtration process for removing blood toxins, comprising:
   passing a fluid containing protein bound and/or middle molecular weight blood toxins through the interior of a hollow fiber membrane;
   during said passage of fluid, providing a sorbent suspension exterior of said hollow fiber membrane; and
   during said passage of fluid, periodically creating pressure differentials across the hollow fiber membrane with a pump so as to cause bi-directional flow in which the fluid or a fraction thereof alternately exits and re-enters the interior of the hollow fiber membrane, wherein said exiting fluid or fraction contains the protein bound and/or middle molecular weight toxins which contact said sorbent suspension so as to effectuate removal of said toxins from said fluid.

19. The process of claim 18 wherein said hollow fiber membrane is a plasmafiltration membrane.

20. The process of claim 19, wherein said fluid is blood.

21. The process of claim 20, wherein said sorbent suspension contains charcoal.

22. The process of claim 18, wherein the fluid contains red blood cells, and wherein the red blood cells are polarized against the hollow fiber membrane during a first flow direction of the bidirectional flow in which the fluid or fraction thereof exits the hollow fiber membrane, and wherein the polarized red blood cells are lifted from the hollow fiber membrane during a second flow direction of the bidirectional flow in which the fluid or fraction thereof re-enters the hollow fiber membrane.

23. A device for removing protein bound and/or middle molecular weight blood toxins from a fluid, comprising:
- a hollow fiber membrane which is permeable to the protein bound and/or middle molecular weight blood toxins, said hollow fiber membrane having an interior for communicating a fluid containing said toxins;
- a sorbent suspension in fluid communication with exterior surfaces of said hollow fiber membrane; and
- an apparatus adapted to create periodic pressure differentials across said membrane so as to cause the fluid or a fraction thereof to alternately exit and re-enter the interior of the follow fiber membrane, wherein said exiting fluid or fraction contains the protein bound and/or middle molecular weight toxins which contact the sorbent suspension so as to effectuate removal of said toxins from said fluid.

24. The device of claim 23, wherein said sorbent suspension contains charcoal, and wherein said apparatus is a pump.

25. The device of claim 23, wherein said hollow fiber membrane is a plasmafiltration membrane.

* * * * *

UNITED STATES PATENT AND TRADEMARK OFFICE
CERTIFICATE OF CORRECTION

PATENT NO : 5,919,369
DATED : July 6, 1999
INVENTOR(S) : Stephen R. Ash

It is certified that error appears in the above-identified patent and that said Letters Patent is hereby corrected as shown below:

In col. 22, line 2, please delete "follow" and insert in lieu thereof —hollow—.

Signed and Sealed this

Twenty-first Day of November, 2000

Attest:

Q. TODD DICKINSON

Attesting Officer

Director of Patents and Trademarks